US005170518A

United States Patent [19]

Warriner

[11] Patent Number: 5,170,518

[45] Date of Patent: Dec. 15, 1992

[54] EMERGENCY EYE AND BODY WASH STATION

[76] Inventor: Joe F. Warriner, 3315 NW. 63, Suite A, Oklahoma City, Okla. 73116

[21] Appl. No.: 804,300

[22] Filed: Dec. 9, 1991

[51] Int. Cl.[5] ........ A01H 33/04

[52] U.S. Cl. ........ 4/620; 239/556

[58] Field of Search ........ 4/620, 638; 239/556 X, 239/587.1; 137/887; 604/294–301

[56] References Cited

U.S. PATENT DOCUMENTS

D. 250,594 12/1978 Gardner ........ D23/34
2,366,427 1/1945 Scheid ........ 239/25
2,474,286 6/1949 Snyder ........ 239/25
3,925,829 12/1975 Bost ........ 4/620
4,627,845 12/1986 De Motte ........ 4/620 X
4,688,276 8/1987 Allison et al. ........ 4/620

OTHER PUBLICATIONS

Journal of Chemical Education, vol. 52, No. 12 (Dec. 1975) p. 810.

*Primary Examiner*—Charles E. Phillips
*Attorney, Agent, or Firm*—Robert K. Rhea

[57] ABSTRACT

An eye and body wash fountain apparatus which can be quickly and easily attached to the water outlet nozzle of a faucet when the need arises for irrigating the eyes, face and body in case of an accident. Water from the faucet nozzle is diverted in dual streams in a forward and upward direction for irrigating the respective eye of a user.

2 Claims, 1 Drawing Sheet

EMERGENCY EYE AND BODY WASH STATION

BACKGROUND OF THE INVENTION

1. Field of the Invention

This invention relates to an eye and body wash fountain apparatus which can be quickly and easily attached to a sink faucet.

Emergency eye wash fountains are required for employee safety in laboratories, factories and warehouses where employees handle corrosive materials which may be injurious to their eyes.

It is also presently a requirement that an eye wash station be provided in dentist offices and it is particularly desirable to have such eye flushing facilities immediately at hand in the chemical laboratories where risk of eye injury rate is high.

2. Description of the Prior Art

Eye wash fountains of various types have been in common use for many years, however such eye wash fountains have usually comprised machined parts involved in mating and mismating apertures for the use of the fountain. These fountains have been provided at stations which are adjacent to but usually removed from the immediate work area.

An example of such fountains is shown by U.S. Pat. No. 3,925,829 comprising a member permanently attached to a faucet outlet which does not normally interfere with the use of faucet but can be quickly adjusted for diverting water from the faucet to a pair of outlets directing water flow upwardly for washing the eyes.

U.S. Pat. No. D. 250,594 similarly discloses a permanently attached faucet eye wash fountain having lateral discharge tubes directing streams of water upwardly for washing the eyes.

Because the need of such facilities is usually infrequent the location thereof is not normally well known to workers located in the above described industrial facilities.

Accordingly this invention provides a simple dual stream directed apparatus not requiring separate faucet attachment parts but which may be quickly and easily attached to a sink faucet outlet for use in washing eyes or other parts of the face.

SUMMARY OF THE INVENTION

A tubular 90° elbow of selected sized is provided at one of its openings with an elastomeric member which frictionally receives in substantially water tight relation the water outlet nozzle of a common sink faucet.

The opposite or other outlet end of the elbow is provided with a cap having a pair of outlet apertures directed upwardly in diverging relation and in a direction opposite the direction of the faucet so that when attached to the faucet by the elastomeric provided end and the faucet cold water lever opened, water is directed upwardly toward the eyes of the user when placed adjacent the outlet end of the elbow.

The principal object of this invention is to provide an apparatus which can be quickly and easily connected to a common sink faucet to convert the faucet to an eye wash fountain.

DESCRIPTION OF THE PREFERRED EMBODIMENTS

Figure 1:
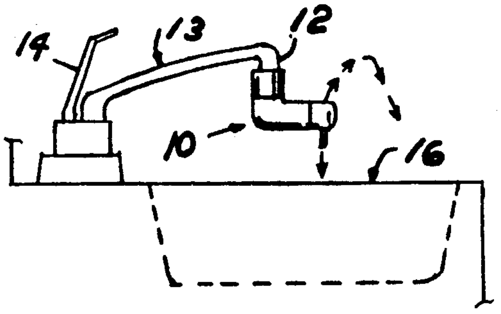
FIG. 1 is a side elevation schematic of my eye and body wash fountain when attached to a sink faucet and in use.
Figure 3:
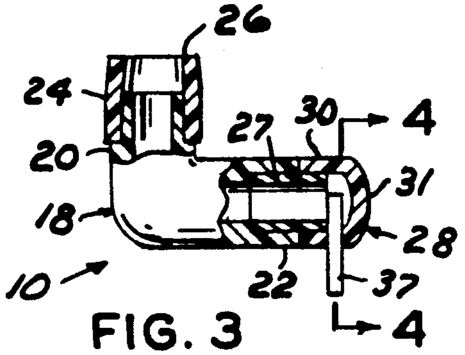
FIG. 3 is a side elevational view, to a larger scale of my eye wash fountain, per se.

Like characters of reference designate like parts in those figures of the drawings in which they occur.

In the drawings:

Referring first to FIG. 1, the reference numeral 10 indicates the device connected with the water outlet nozzle 12, which may be an aerator, of a faucet 13 connected with a source of drinking water and controlled by a handle 14 for normally discharging water into a lavatory or sink 16.

The device 10 is formed by a street elbow 18 having male and female inlet and outlet end portions 20 and 22, respectively, disposed in right angular relation.

The inlet end portion 20 frictionally receives one end of a relatively short elastomeric sleeve 24 having its other or open end 26 dimensioned for frictionally receiving the nozzle 12 of the faucet 13 so that water is directed through the elbow toward its outlet end portion 22.

The outlet end portion 22 of the elbow frictionally receives one end portion of a short sleeve 27 having its other end closed by a manually rotatable pipe cap 28 having a peripheral wall 30 and an end wall 31.

Figure 2:
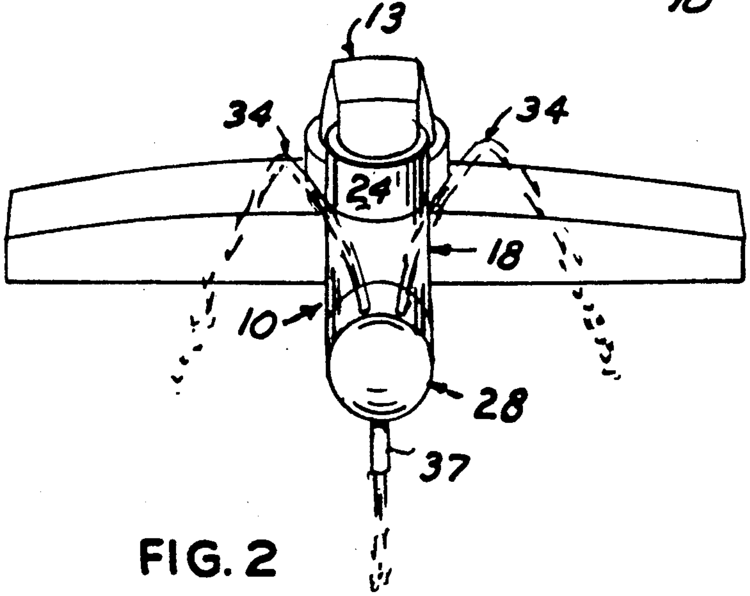
FIG. 2 is a fragmentary perspective view, to a larger scale, taken from the right side of FIG. 1.
Figure 4:
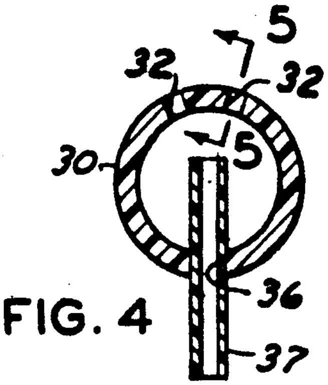
FIG. 4 is a vertical cross sectional view, taken substantially along the line 4—4 of FIG. 3; and, FIG. 5 is a fragmentary vertical cross sectional view, to a further enlarged scale, taken substantially along the line 5—5 of FIG. 4.
Figure 5:
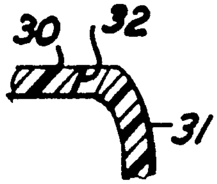

The upwardly disposed portion of the peripheral wall 30 is provided with a pair of radial laterally spaced upwardly diverging bores 32 adjacent the inner surface of the cap wall 31 (FIG. 5). Both bores 32 being angularly drilled to disposed their respective axis inclined in an upward and forward direction toward a user when standing facing the faucet 13 for the purpose of directing a pair of water streams 34 (FIG. 2) in diverging relation toward the user.

A third radial bore 36 extends through the cap peripheral wall 30 adjacent the end wall 31 and diametrically opposite the bores 32. The bore 36 coaxially receives one end portion of a tube 37 and provides an upwardly directed water stream for face or body washing when the cap has been manually angularly rotated 180° from its eye washing position.

In practice, the device 10, a length of vinyl tubing, for coaxial frictional connection with the tube 37, and a plastic sanitary bag, neither being shown, are placed adjacent a sink for emergency use .

Obviously the invention is susceptible to changes or alterations without defeating its practicability. Therefore, I do not wish to be confined to the preferred embodiment shown in the drawings and described herein.

I claim:

1. An eye wash fountain attachment for a water faucet having a downwardly open nozzle, comprising:

an L-shaped tubular body having a diameter and having an inlet end and an outlet end; means for coaxially connecting the inlet end of said body to said nozzle;

a cap element rotatably secured to the outlet end of said body, said cap having a peripheral wall and an end wall and having a pair of spaced-apart bores diverging in an upward direction in its peripheral wall adjacent the end wall to produce two streams of water in an upwardly diverging cooperating relation such that one stream may strike one eye of the user while the other stream strikes the other eye of the user is disposed in one position; and, a relatively small diameter tube, when compared with the diameter of said body, extending through the cap peripheral wall substantially diametrically opposite the pair of bores for directing a water stream vertically upward when the cap is angularly rotated to another position.

2. The eye wash fountain according to claim 1 in which the coaxial connecting means includes:

an elastomeric tube extending between and axially surrounding at its respective end portion the faucet nozzle and the body inlet end portion.

* * * * *